(12) United States Patent
Al-Shehry

(10) Patent No.: US 8,852,651 B1
(45) Date of Patent: Oct. 7, 2014

(54) PLANT EXTRACTS FOR USE IN ENHANCING IMMUNE SYSTEM AND BRAIN MODULATION

(76) Inventor: Ahmad Hamden Al-Shehry, Almadinah (SA)

(*) Notice: Subject to any disclaimer, the term of this patent is extended or adjusted under 35 U.S.C. 154(b) by 0 days.

(21) Appl. No.: 13/569,470

(22) Filed: Aug. 8, 2012

Related U.S. Application Data

(60) Provisional application No. 61/625,240, filed on Apr. 17, 2012.

(51) Int. Cl.
*A61K 36/00* (2006.01)
(52) U.S. Cl.
USPC .......................................................... 424/725
(58) Field of Classification Search
None
See application file for complete search history.

(56) References Cited

U.S. PATENT DOCUMENTS

2005/0152852 A1* 7/2005 Nishimura et al. ............. 424/50
2012/0201909 A1* 8/2012 Sanabria ....................... 424/727

FOREIGN PATENT DOCUMENTS

KR 2011067828 A * 6/2011

OTHER PUBLICATIONS

Yemeni Sidr Honey (Yemeni Sidr Honey VS New Zealand Manuka Honey? website is http://www.yeminisidrhoney.com/, see website article published on Sep. 22, 2008).*

* cited by examiner

*Primary Examiner* — Chris R Tate
*Assistant Examiner* — Randall Winston
(74) *Attorney, Agent, or Firm* — Charles L. Thoeming

(57) ABSTRACT

A pharmaceutical composition, nutraceutical composition or functional food product comprising a compound or a mixture of compounds selected from the group consisting of Sidr honey, Ajwa Al-Madinah, Sannoot, Senna, Indian Costus Root, Nuclei dates, Black Seed, and Zamzam Water, as active ingredient together with a pharmaceutically acceptable diluents or carrier for treatment or prophylaxis of one or more of the following symptoms or disorders: diminished immune system, anxiety, memory deficits and dysfunctions, lack of concentration, diminished emotional well-being, low spirits, sexual dysfunction, impotence, or lack of appetite. Methods of treatment are also presented.

12 Claims, No Drawings

PLANT EXTRACTS FOR USE IN ENHANCING IMMUNE SYSTEM AND BRAIN MODULATION

CROSS-REFERENCES TO RELATED APPLICATIONS

This United States non-provisional patent application is based upon and claims the filing date of U.S. provisional patent application Ser. No. 61/625,240 filed Apr. 17, 2012.

STATEMENT REGARDING FEDERALLY SPONSORED RESEARCH OR DEVELOPMENT

None.

REFERENCE TO A MICRO-FICHE APPENDIX

None.

TECHNICAL FIELD

The invention relates to natural compounds or derivatives of them, to compositions comprising them, and/or to their use as modulating agents in humans for enhancing the immune system, lifting the mood, increasing sexual function, increasing sexual performance and libido, or positively affecting motivation.

BACKGROUND OF THE INVENTION

A further objective of the plant extracts for use in enhancing the immune system and brain modulation is to provide natural components with good nutritional value.

Yet another principal objective of plant extracts for use in enhancing the immune system and brain modulation is to provide a beneficial health food for the human body.

Another objective of the plant extracts for use in enhancing the immune system and brain modulation is to provide a beneficial health food for the human body that does not have any preservatives and that has a shelf life of more than eighteen months.

A further objective of the plant extracts for use in enhancing the immune system and brain modulation is to administer a therapeutically effective amount of a natural or organic, functional food product, without the presence of toxic substances or materials, in persons for the treatment or prophylaxis of one or more of the following symptoms or disorders: diminished immune system, anxiety, memory deficits and dysfunctions, lack of concentration, diminished emotional well-being, low spirits, sexual dysfunction, impotence, or lack of appetite.

A further objective of the plant extracts for use in enhancing the immune system and brain modulation is to administer a therapeutically effective amount of a natural or organic, functional food product having an acceptable, pleasant taste.

A further objective of the plant extracts for use in enhancing the immune system and brain modulation is to administer a therapeutically effective amount of a natural or organic, functional product that provides benefits for the human body and that has no negative side effects.

Another objective of the plant extracts for use in enhancing the immune system and brain modulation is to provide a therapeutically effective skin cream or ointment.

DISCLOSURE OF INVENTION

It is an objective of the present invention to make available new compounds or compositions useful in the treatment (including therapy and prophylaxis) of various disorders or improving the immune response system and neurological or mental situation in the human body.

Surprisingly, extracts obtained from Sidr honey, Aiwa Al-Madinah, Sannoot, Senna, Indian Costus Root, Nuclei dates, Black Seed, and Zamzam Water derivatives as well as some purified compounds from this class out of such extracts can be shown to exhibit an enhancing effect on the immune system and/or neurotransmitter concentration by unknown mechanism, as is described in more detail below.

Even more surprisingly, the compounds cannot be found in the separate use of these ingredients, and thus a new and improved method of treatment, compound or mixture of compounds, and functional food product is made available in the treatment of the immune system and neurological and/or mental condition of humans.

BRIEF DESCRIPTION OF DRAWINGS

There are no drawings.

BEST MODE FOR CARRYING OUT THE INVENTION

An embodiment of plant extracts for use in enhancing the immune system and brain modulation provides a method of treatment comprising: providing a compound or mixture of compounds selected from the group consisting of Sidr honey, Ajwa Al-Madinah, Sannoot, Senna, Indian Costus Root, Nuclei dates, Black Seed, and Zamzam Water, and administering prophylactically and/or therapeutically effective amount of the compound or mixture of compounds to a patient in need thereof for treatment of one or more of the following conditions: diminished immune system, anxiety, memory deficits and dysfunctions, lack of concentration, diminished emotional well-being, low spirits, sexual dysfunction, impotence, or lack of appetite.

Senna is also known as Cassia senna, tinnevelly senna, India senna, Alexandrian senna, and Khartoum senna.

Sannoot is also known as Fennel (*Foeniculum vulgare*), a plant species in the genus *Foeniculum* (treated as the sole species in the genus by most botanists). It is a member of the familyApiaceae (formerly the Umbelliferae). It is a hardy, perennial, umbelliferous herb, with yellow flowers and feathery leaves. It is indigenous to the shores of the Mediterranean, but has become widely naturalised in many parts of the world, especially on dry soils near the sea-coast and on riverbanks. It is a highly aromatic and flavorful herb with culinary and medicinal uses, and, along with the similar-tasting anise, is one of the primary ingredients of absinthe. Florence fennel or finocchio is a selection with a swollen, bulb-like stem base that is used as a vegetable.

*Costus* is a genus of perennial tropical herbaceous plants from the costus family (Costaceae). They are often characterized and distinguished from relatives such as *Zingiber* (true ginger) by their spiraling stems. The genus as a whole is thus often called spiral gingers, but this can also refer to *C. barbatus* specifically. *Costus spectabilis* the floral emblem of Nigeria; its flowers are represented (erroneously in red instead of yellow color) on its coat of arms. It is important not to confuse "Costus speciousus, *C. spectabilis* etc. with the herb known by the common name 'costus'. Some species are of importance to herbivores, such as caterpillars of the Restricted Demon (*Notocrypta curvifascia*) which feed on Crape Ginger (*C. speciosus*). The Crape Ginger is also a source of diosgenin, a compound that has been used for the commercial production of various steroids, such as progesterone. In Trinidad and Tobago, a mix of *Costus scaber* juice and crushed *Renealmia alpinia* berries has been used to treat dogs bitten by snakes.

In English, *Nigella sativa* seed is variously called fennel flower, nutmeg flower, Roman coriander, blackseed or black caraway. Other names used, sometimes misleadingly, are onion seed and black sesame, both of which are similar-looking, but unrelated. The seeds are frequently referred to as black cumin (as in Assamese: kaljeera or kolajeera or Bengali kalo jeeray), In south Indian language Kannada it is called "Krishna Jeerige", but this is also used for a different spice, *Bunium persicum* (=*Carum bulbocastanum*).

An embodiment of plant extracts for use in enhancing the immune system and brain modulation consists of eight varieties mixing with the Sidr Honey as follows:

Sidr Honey—250 Grams;
Ajwa Al-Madinah, kneaded until it becomes a dough—3 Grams;
Sannoot (Fennel), grinding the seed of this herb to a powder then added to the dough—6 Grams;
Senna, grinding this herb's papers without it sticks and seeds—3 Grams;
Indian Costus Root, grinding the roots to a powder—3 Grams;
Nuclei dates, grinding to be a powder—3 Grams;
Black Seed, grinding to a powder—3 Grams; and
Zamzam Water—1 ml.

An embodiment of plant extracts for use in enhancing the immune system and brain modulation provides a method of treatment comprising: providing a compound or mixture of compounds selected from the group consisting of Sidr honey, Ajwa Al-Madinah, Sannoot, Senna, Indian Costus Root, Nuclei dates, Black Seed, and Zamzam Water, and administering prophylactically and/or therapeutically effective amount of the compound or mixture of compounds to a patient in need thereof for treatment of one or more of the following conditions: diminished immune system, anxiety, memory deficits and dysfunctions, lack of concentration, diminished emotional well-being, low spirits, sexual dysfunction, impotence, or lack of appetite, and wherein said compound or a mixture of compounds comprises at least 92 percent by weight Sidr honey, at least 1 percent by weight Ajwa Al-Madinah, at least 2 percent by weight Sannoot, at least 1 percent by weight Senna, at least 1 percent by weight Indian Costus Root, at least 1 percent by weight Nuclei dates, at least 1 percent by weight Black Seed, and at least 1 milliliter Zamzam Water based on the total weight of the compound or mixture.

An embodiment of plant extracts for use in enhancing the immune system and brain modulation includes the step of administering prophylactically and/or therapeutically effective amount of the compound or mixture of compounds to a patient in need thereof comprises at least one daily dosage of the compound or mixture of compounds.

An embodiment of plant extracts for use in enhancing the immune system and brain modulation includes the step of administering prophylactically and/or therapeutically effective amount of the compound or mixture of compounds to a patient in need thereof comprises administering a therapeutically effective amount for the treatment or prophylaxis of one or more of the following symptoms or disorders: diminished immune system, anxiety, memory deficits and dysfunctions, lack of concentration, diminished emotional well-being, low spirits, sexual dysfunction, impotence, or lack of appetite.

An embodiment of plant extracts for use in enhancing the immune system and brain modulation includes a compound or a mixture of compounds selected from the group consisting of Sidr honey, Ajwa Al-Madinah, Sannoot, Senna, Indian Costus Root, Nuclei dates, Black Seed, and Zamzam Water, as active ingredients together with a pharmaceutically acceptable diluent or carrier for mood-lifting in healthy persons or one or more of the treatment or prophylaxis of one or more of the following symptoms or disorders: diminished immune system, anxiety, memory deficits and dysfunctions, lack of concentration, diminished emotional well-being, low spirits, sexual dysfunction, impotence, or lack of appetite, wherein the functional food product comprises 0.001-92% by weight of Sidr Honey.

An embodiment of plant extracts for use in enhancing the immune system and brain modulation includes 0.001 to 1% by weight of ingredients selected from the group consisting of Ajwa Al-Madinah, Senna, Indian Costus Root, Nuclei dates, and Black Seed.

An embodiment of plant extracts for use in enhancing the immune system and brain modulation includes 0.001 to 2% by weight of Sannoot.

An embodiment of plant extracts for use in enhancing the immune system and brain modulation includes a functional food product that further provides one or more common food ingredients selected from the group consisting of flavours, sugars, minerals, vitamins, stabilizers, thickeners, dietary fibers, protein, and amino acids.

An embodiment of plant extracts for use in enhancing the immune system and brain modulation includes a functional food product that further provides one or more additives selected from the group consisting of thickeners, colouring agents, bulking agents, polyols, xylitol, mannitol, maltitol, preservatives, sodium or potassium benzoate, sodium or calcium carbonate; antioxidants, ascorbic acid, carotionoids, tocopherols or polyphenols, mono-, oligo- or polysaccharides, glucose, fructose, sucrose, soyoligosaccharides, xylo-oligosaccharides, galacto-oligosaccharides, artificial or natural non- or low-caloric sweeteners, aspartame, acesulfame, acidifiers in the form of edible acids, citric acids, acetic acid, lactic acid, adipic acid; flavours, emulsifiers, diluents, maltodextrose, wetting agents, glycerol, stabilizers, coatings, isotonic agents, and absorption promoting or delaying agents.

An embodiment of plant extracts for use in enhancing the immune system and brain modulation includes a functional food product that is selected from the group consisting of fruit or juice products, concentrates of fruit or juice products, lemonades, dairy type products, frozen confectionary products, baked goods, spreads, margarine, butter, peanut butter, honey, snacks, pasta products, other cereal products, ready-to-serve-dishes, frozen food, tinned food, syrups, sauces, fillings, dips, chewing gums, sherbet, spices, cooking salt, and instant drink powders.

An embodiment of plant extracts for use in enhancing the immune system and brain modulation includes a pharmaceutical composition, nutraceutical composition or functional food product comprising a compound or a mixture of compounds selected from the group consisting of Sidr honey, Ajwa Al-Madinah, Sannoot, Senna, Indian Costus Root, Nuclei dates, Black Seed, and Zamzam Water, as active ingredient together with a pharmaceutically acceptable diluent or carrier for treatment or prophylaxis of one or more of the following symptoms or disorders: diminished immune system, anxiety, memory deficits and dysfunctions, lack of concentration, diminished emotional well-being, low spirits, sexual dysfunction, impotence, or lack of appetite.

An embodiment of plant extracts for use in enhancing the immune system and brain modulation includes a nutraceutical composition in the form of granules, tablets, pills, capsules, salves, lotions, or suspensions.

An embodiment of plant extracts for use in enhancing the immune system and brain modulation includes a nutraceutical composition that includes one or more other active agents, wherein the other active agents are one or more of phytotherapeutics or other common pharmaceuticals, and wherein said composition is in the form of tablets, hard gelatine capsules, soft gelatine capsules, pills, sachets, powders, granules, solutions, suspensions, ointment, lotions, creams, hydrogels, lipogels, micronized powders, sprays, aerosols, or plasters.

An embodiment of plant extracts for use in enhancing the immune system and brain modulation includes a pharmaceutical composition or nutraceutical composition for topical administration to the skin or mucous membranes, and the composition is in the form of an ointment, tincture, cream, gel, solution, lotion; nasal spray; aerosol, dry powder for inhalation, suspension, shampoo, hair soap, or perfume.

An embodiment of plant extracts for use in enhancing the immune system and brain modulation includes a pharmaceutical composition or nutraceutical composition for topical administration to the skin or mucous membranes, and the compound or a mixture of compounds for each such composition is at 0.3 to 20.0 percent by weight based on the total weight of the pharmaceutical composition, nutraceutical composition or functional food product.

While the present disclosure has been described and illustrated herein by references to various specific materials, procedures and examples, it is understood that the disclosure is not restricted to the particular combinations of material and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

I claim:

1. A functional food product for the treatment of a diminished immune system, wherein the functional food product comprises:
    a) 0.001 to 92% by weight of Sidr Honey;
    b) 0.001 to 1% by weight of an ingredient selected from the group consisting of Ajwa Al-Madinah, Senna, Indian Costus Root, Nuclei dates and Black seed;
    c) 0.001 to 2% by weight of Sanoot; and
    d) a pharmaceutical acceptable diluent or carrier.

2. The functional food product according to claim 1, wherein the functional food product further comprises one or more food ingredients selected from the group consisting of flavors, sugars, minerals, vitamins, stabilizers, thickeners, dietary fibers, protein, and amino acids.

3. The functional food product according to claim 1, wherein the functional food product further comprises one or more additives selected from the group consisting of thickeners, coloring agents, bulking agents, polyols, xylitol, mannitol, maltitol, preservatives, sodium or potassium benzoate, sodium or calcium carbonate, antioxidants, ascorbic acid, carotionoids, tocopherols or polyphenols, mono-, oligo- or polysaccharides, glucose, fructose, sucrose, soyoligosaccharides, xylo-oligosaccharides, galacto-oligosaccharides, artificial or natural non- or low-caloric sweeteners, aspartame, acesulfame, acidifiers in the form of edible acids, citric acids, acetic acid, lactic acid, adipic acid, flavors, emulsifiers, diluents, maltodextrose, wetting agents, glycerol, stabilizers, coatings, isotonic agents, and absorption promoting or delaying agents.

4. The functional food product according to claim 1, wherein the functional food product is selected from the group consisting of fruit or juice products, concentrates of fruit or juice products, lemonades, dairy type products, frozen confectionary products, baked goods, spreads, margarine, butter, peanut butter, honey, snacks, pasta products, other cereal products, ready-to-serve-dishes, frozen food, tinned food, syrups, sauces, fillings, dips, chewing gums, sherbet, spices, cooking salt and instant drink powders.

5. A pharmaceutical composition or nutraceutical composition for the treatment of a diminished immune system, wherein the pharmaceutical composition, nutraceutical composition or functional food product comprises:
    a) 0.001 to 92% by weight of Sidr Honey;
    b) 0.001 to 1% by weight of an ingredient selected from the group consisting of Ajwa Al-Madinah, Senna, Indian Costus Root, Nuclei dates and Black seed;
    c) 0.001 to 2% by weight of Sanoot; and
    d) a pharmaceutically acceptable diluent or carrier.

6. The nutraceutical composition according to claim 5, wherein the composition is in the form of granules, tablets, pills, capsules, salves, lotions or suspensions.

7. The pharmaceutical composition according to claim 5, wherein the composition further comprises one or more active ingredients selected from the group consisting of one or more phytotherapeutics and common pharmaceuticals and wherein the composition is in the form of tablets, hard gelatin capsules, soft gelatin capsules, pills, sachets, powders, granules, solutions, suspensions, ointment, lotions, creams, hydrogels, lipogels, micronized powders, sprays, aerosols or plasters.

8. The composition according to claim 5, wherein the pharmaceutical composition or nutraceutical composition is for topical administration to the skin or mucous membranes and is in the form of an ointment, tincture, cream, gel, solution, lotion, nasal spray, aerosol, dry powder for inhalation, suspension, shampoo, hair soap or perfume.

9. A functional food product for the treatment of a diminished immune system, wherein the functional food product comprises:
    a) 250 grams of Sidr Honey;
    b) 3 grams of Ajwa AL-Madinah, knead until it becomes a dough;
    c) 6 grams of Sanoot (Fennel), the seed of this herb ground to a powder then added to the Ajwa Al-Madinah dough;
    d) 3 grams of Senna, this herb's papers ground without it sticks and seeds;
    e) 3 grams of Indian Costus Root, the root ground to a powder;
    f) 3 grams of Nuclei dates, ground to a powder;
    g) 3 grams of Black Seed, ground to a powder; and
    h) 1 milliliter of Zamzam Water.

10. The functional food product according to claim 9, wherein the functional food product further comprises one or more food ingredients selected from the group consisting of flavors, sugars, minerals, vitamins, stabilizers, thickeners, dietary fibers, protein, and amino acids.

11. The functional food product according to claim 9, wherein the functional food product further comprises one or more additives selected from the group consisting of thickeners, coloring agents, bulking agents, polyols, xylitol, mannitol, maltitol, preservatives, sodium or potassium benzoate, sodium or calcium carbonate, antioxidants, ascorbic acid, carotionoids, tocopherols or polyphenols, mono-, oligo- or polysaccharides, glucose, fructose, sucrose, soyoligosaccharides, xylo-oligosaccharides, galacto-oligosaccharides, artificial or natural non- or low-caloric sweeteners, aspartame, acesulfame, acidifiers in the form of edible acids, citric acids, acetic acid, lactic acid, adipic acid, flavors, emulsifiers, diluents, maltodextrose, wetting agents, glycerol, stabilizers, coatings, isotonic agents, and absorption promoting or delaying agents.

12. The functional food product according to claim 9, wherein the functional food product is selected from the group consisting of fruit or juice products, concentrates of fruit or juice products, lemonades, dairy type products, frozen confectionary products, baked goods, spreads, margarine, butter, peanut butter, honey, snacks, pasta products, other cereal products, ready-to-serve-dishes, frozen food, tinned food, syrups, sauces, fillings, dips, chewing gums, sherbet, spices, cooking salt and instant drink powders.

* * * * *

UNITED STATES PATENT AND TRADEMARK OFFICE
CERTIFICATE OF CORRECTION

| | | |
|---|---|---|
| PATENT NO. | : 8,852,651 B1 | Page 1 of 1 |
| APPLICATION NO. | : 13/569470 | |
| DATED | : October 7, 2014 | |
| INVENTOR(S) | : Ahmad Hamdan M. Alshehri | |

It is certified that error appears in the above-identified patent and that said Letters Patent is hereby corrected as shown below:

On the Title page, the spelling of the Inventor's name: "Ahmad Hamden Al-Shehry" should be changed to -- Ahmad Hamdan M. Alshehri --

Signed and Sealed this
Twenty-ninth Day of March, 2016

Michelle K. Lee
*Director of the United States Patent and Trademark Office*